United States Patent [19]

Desbordes et al.

[11] Patent Number: 5,123,953

[45] Date of Patent: Jun. 23, 1992

[54] DIHALOGENATED HERBICIDAL SULPHONES

[75] Inventors: Philipe Desbordes, Lyons; Michel Euvrard, Fontaines sur Saone; François De Reinach Hirtzbach, Lyons, all of France; Christopher Pearson, Hertford, Great Britain

[73] Assignee: Rhone-Poulenc Agrochimie, Lyons, France

[21] Appl. No.: 507,664

[22] Filed: Apr. 10, 1990

[30] Foreign Application Priority Data

Apr. 10, 1989 [FR] France ............... 89 04940

[51] Int. Cl.$^5$ ............... A01N 31/08; A01N 43/40
[52] U.S. Cl. ............... 71/94; 71/98; 71/103; 568/34; 568/35; 568/27; 568/56; 546/339
[58] Field of Search ............... 71/103, 98, 94; 568/34, 568/35, 27, 56

[56] References Cited

U.S. PATENT DOCUMENTS

| | | | |
|---|---|---|---|
| 3,634,485 | 1/1972 | Howe et al. ............... | 260/465 |
| 4,677,128 | 6/1987 | Place et al. ............... | 514/277 |
| 4,678,811 | 7/1987 | Franke et al. ............... | 514/721 |

FOREIGN PATENT DOCUMENTS

| | | | |
|---|---|---|---|
| 0326170 | 8/1989 | European Pat. Off. | |
| 1087879 | 10/1967 | United Kingdom ............... | 568/34 |
| 2069492 | 8/1981 | United Kingdom | |
| 2197313 | 5/1988 | United Kingdom ............... | 568/34 |

OTHER PUBLICATIONS

Paquette, Leo A., "The Base-Induced Rearrangement of α-Halo Sulfones", Accounts of Chemical Research, vol. 1 No. 7, pp. 209-216 (1968).
Schmid, et al., Can. J. Chem., 1974, 52, 1807-1812.

Primary Examiner—Joseph Paul Brust
Assistant Examiner—Jacqueline Haley
Attorney, Agent, or Firm—Scully, Scott, Murphy & Presser

[57] ABSTRACT

Compounds of formula:

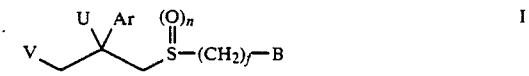

in which:
n=0, 1, 2
f=0, 1
Ar is an optionally substituted phenyl or pyridyl group
U a chlorine or bromine atom
V a bromine or chlorine or iodine atom
B is $C_1$-$C_{10}$ alkyl, $C_3$-$C_{10}$ cycloalkyl, which are optionally substituted by 1 to 6 halogen atoms, phenyl or pyridyl or oxidized pyridyl, which are optionally substituted.

Use of these compounds as herbicides which are selective but especially antigraminaceous at preemergence.

8 Claims, No Drawings

DIHALOGENATED HERBICIDAL SULPHONES

The invention relates to new compounds, to their use as herbicides especially in the form of a herbicidal composition, and to a process for controlling weeds with the aid of these compounds or of these compositions.

An objective of the present invention is therefore to propose compounds which can be used as herbicides in pre- or postemergence Another objective of the present invention is to propose compounds which can be used as antigramineaceous herbicides in pre- or postemergence.

Another objective of the present invention is to propose compounds which can be used in pre- or postemergence as selective herbicides for corn and many dicotyledon crops (especially soya, rape, sunflower, cotton) and other monocotyledon crops (wheat, rice).

GENERAL DEFINITION OF THE INVENTION

Compounds of formula

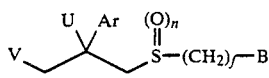

in which:
n = 0, 1, 2
f = 0, 1. Ar is chosen from the groups

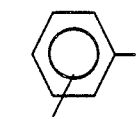

1-Ar

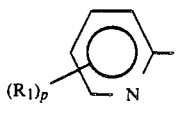

2-Ar

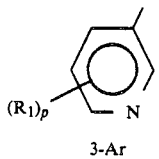

3-Ar

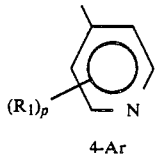

4-Ar

U being a bromine or chlorine atom,
V being a bromine, chlorine or iodine atom,
$R_1$ being a halogen atom (especially Cl or Br or F), a $C_1$–$C_4$ alkyl, $C_1$–$C_4$ alkoxy, $C_1$–$C_4$ haloalkyl, $C_1$–$C_4$ haloalkoxy, nitro or cyano group, $C_6$–$C_{10}$ aryl (especially phenyl or naphthyl), $C_7$–$C_{11}$ aralkyl (especially benzyl), $C_6$–$C_{10}$ aryloxy (especially phenoxy or naphlhoxy) optionally substituted by 1 or 2 halogen atoms or $C_7$–$C_{11}$ aralkyloxy (especially benzyloxy) optionally substituted by 1 or 2 halogen atoms, m = 0, 1, 2, 3, 4, 5, p = 0, 1, 2, 3, 4, the various radicals $R_1$ being identical or different when m or p is greater than or equal to 2, B is chosen from $C_1$–$C_{10}$ alkyl and $C_3$–$C_{10}$ cycloalkyl groups, these groups being optionally substituted by 1 to 6 halogen atoms or chosen from the groups

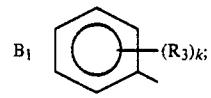

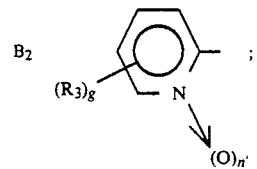

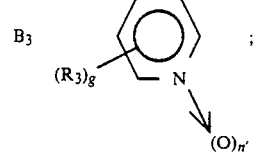

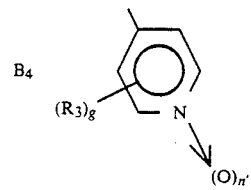

$R_3$ having one of the meanings shown for $R_1$ or $NR_4R_5$, $S(O)_hR_6$, $(C=O)R_7$, $R_4$ and $R_5$, which are identical or different, are H, $C_1$–$C_4$ alkyl or $C_6$–$C_{10}$ aryl, $R_6$ is $C_1$–$C_4$ alkyl, $R_7$ is $C_1$–$C_4$ alkyl, $C_1$–$C_4$ alkoxy, $C_1$–$C_4$ haloalkoxy or $NR_9R_{10}$, $R_9$ and $R_{10}$, which are identical or different, are H or $C_1$–$C_4$ alkyl, the varius radicals $R_3$ being identical or different when
k or g is greater than or equal to 2,
k = 0, 1, 2, 3, 4, 5, g = 0, 1, 2, 3, 4,
h = 0, 1, 2,
n = 0, 1.
The aliphatic groups may be linear or branched.

PREFERRED ALTERNATIVE FORMS

Depending on the preferred embodiments, the following alternative forms will be chosen, taken in combination or otherwise: n = 2, U and V = Br, m smaller than or equal to 3, p smaller than or equal to 2, k smaller than or equal to 2, g smaller than or equal to 1, $R_1$ is halogen, nitro, trifluoromethyl, methoxy or methyl.

The compounds of formula (I) and the compounds which may be employed as intermediates in the processes of preparation, and which will be defined when these processes are described, can exist in one or more isomeric forms, depending on the number of asymmetric centres in the molecule. The invention consequently relates both to all the optical isomers and to their racemic mixtures and the corresponding diastereoisomers. The separation of the diastereoisomers and/or of the optical isomers can be carried out according to methods which are known per se.

PROCESSES FOR THE PREPARATION OF THE COMPOUND OF FORMULA (I)

The compounds of formula (I) in which n=0, 1, 2, the other substituents having the same definition as that shown in the general definition of the invention, may be prepared by bringing a compound of formula:

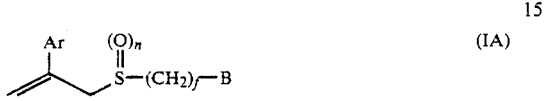

in which Ar, n, f and B have the same meaning as in the general definition of the invention, into contact with halides UV like chlorine (U=Cl, V=Cl), bromine (U=Br, V=Br), chlorine iodide (U=Cl, V=I), bromine iodide (U=Br, V=I) or chlorine bromide (U=Cl, V=Br), in an aprotic inert solvent such as chloroform, carbon tetrachloride, tetrahydrofuran, dimethoxyethane or acetonitrile, in the presence or otherwise of an acid such as acetic acid or hydrochloric acid at a temperature of $-78°$ C. to $60°$ C. (preferably $0°$ C. to $20°$ C.) and in a molar ratio IA:UV of between 1 and 5 (preferably 1 and 2). This reaction is known especially from J. March, "Advanced Organic Chemistry", publ. McGraw-Hill (1985), p. 724–726, S. Akiyoshi and K. Okuno, J. Amer. Chem Soc. (1952), 74, 5759 and F. G. Weber, Tetrahedron (1969), 25, 4283.

These same compounds of formula (I) in which n=0, 1 or 2, the other substituents having the same definition as that shown in the general definition of the invention, can also be prepared by the action on a compound of formula (IA) where the substituents have the same meaning as in the general definition of the invention, of a halogenating agent ZV, V being the chlorine or bromine atom and Z an acetamido radical, such as N-haloacetamide or N-halosuccinimide in the presence of a donor of a halide anion U, U being the chlorine or bromine atom, such as the hydrogen halide acids HU, ammonium halides $(R)_4NU$, R being an alkyl radical, or the salts MU, M being an atom of an alkali or alkaline-earth metal or a silver atom in an inert solvent such as methylene chloride, chloroform, acetonitrile, dimethoxyethane or acetic acid at a temperature of $-78°$ C. to $60°$ C. (preferably $0°$ C. to $20°$ C.) and in a molar ratio IA:ZV:U of between 1:1:1 and 1:5:100 (preferably 1:2:5).

This reaction is known especially from J. March, ibid. p. 725, R. E. Buckles and J. W. Long, J. Amer. Chem. Soc (1959), 81, 2191, A. Marquet and J. Jacques, Tetrahedron Letters (1959), 9, 24 and C. H. Robinson et al., J. Amer. Chem. Soc. (1959), 81, 2191.

The compounds of formula (I) in which n=0 or 1, the other substituents having the same definition as that shown in the general definition of the invention, can be oxidized to a sulphoxide (n=1) by one equivalent of oxidizing agent at a temperature of $-70°$ C. to $5°$ C. (generally $0°$ C.) or can be oxidized to a sulphone (n=2) by two or more equivalents of oxidizing agent at a tempera ture of $0°$ C. to $60°$ C. (generally $10°$ C. to $30°$ C.) by many oxidizing agents, such as $KMnO_4$, $H_2O_2$, $CH_3CO_3H$, perbenzoic acids, $KHSO_5$, and others, by following very many known methods, J. March, ibid. p. 1089–1090 and B. M. Trost and R. Braslau, J. Org. Chem. (1988), 53, 532.

PROCESS FOR THE PREPARATION OF THE COMPOUND OF FORMULA IA

Method A

The compounds of formula (IA) in which n=2, the other substituents having the same definition as that shown in the general definition of the invention, can be obtained by bringing a compound of formula

in which Ar, $R_1$ and m or p have the same meaning as in the general definition of the invention, and T is a chlorine or bromine atom, into contact with a compound of formula:

$$MSO_2(CH_2)_f B \quad (III)$$

f and B having the same definition as that shown in the definition of the invention, M being an atom of an alkali or alkaline-earth metal (expecially Li, K, Na).

The reaction is generally performed in a dipolar aprotic solvent, especially dimethylformamide or N-methylpyrrolidone, or in water in a mixture in the proportions of 5/95 to 90/10 (preferably 10/90 to 50/50) with a water-soluble solvent such as alcohols, acetone, acetonitrile or dimethoxy-ethane, in the presence or otherwise of a catalytic or other quantity of alkali metal iodide, in the presence or absence of a catalytic quantity of a phase transfer agent such as tetrabutylammonium halides, at a temperature of between $25°$ C. and $150°$ C. (preferably $60°$ C. to $120°$ C.) and in a molar ratio II:III of between 1 and 10 (preferably 1 and 2).

This reaction is known especially from J. March, ibid. p. 363. The compounds of formula (II) where T is chlorine and Ar is 1-Ar (phenyl nucleus) are prepared by chlorination of a 2-phenyl-1-propene compound of formula:

in which Ar is 1-Ar (phenyl nucleus), $R_1$ and m having the same meaning as in the definition of the general fcrmula, by means of the reactant $Ca(OCl)_2/CO_2$. This reaction is described by S. G. Hegde and J. Wolinsky, Tetrahedron Letters (1981), 22, 5019.

These same compounds of formula (II) where T is chlorine and Ar is 1-Ar (phenyl nucleus) can be prepared by chlorination of the compounds of formula (IV) by means of the $SO_2Cl_2/Na_2CO_3$ reactant according to M. Bulliard et al., Tetrahedron Letters (1989), 30, 5767.

The compounds of formula (II) where T is chlorine, Ar having the same definition as that shown in the general definition of the invention, can also be prepared by chlorination of the abovementioned compounds of formula (IV) using N-chlorosuccinimide in the presence of bisaryl diselenide according to the process of K. B. Sharpless and T. Hori, J. Org. Chem. (1979), 44, 4204.

The compounds of formula (II) where T is chlorine or bromine, Ar having the same definition as that shown in the general definition of the invention, can also be prepared by thermal or photochemical radical halogenation of the compound of formula (IV) using N-halosuccinimide in an aprotic solvent such as carbon tetrachloride or in the absence of solvent, with or without a free-radical initiator, at a temperature of 20° C. to 170° C. (preferably 80° C. to 100° C.), according to S. F. Reed, J. Org. Chem. (1965), 30, 3258. They can also be prepared by halogenation of the compounds of formula (II) where T is OH, Ar having the same definition as that shown in the general definition of the invention, with a halogenating agent such as $SOCl_2$, $POCl_3$, $PBr_3$, J. March, ibid. p. 382-384, or with the $LiCl/CH_3SO_2Cl$/collidine reactant according to E. W. Collington and A. I. Meyers, J. Org. Chem. (1971), 36, 3044.

The compounds of formula (II) where T is OH, Ar having the same definition as that shown in the general definition of the invention, can be prepared by allylic oxidation of the compound of formula (IV) using selenium oxide, catalytic or otherwise, in the presence of an oxidizing agent such as tert-butyl hydroperoxide, in an inert solvent such as halogenated solvents (preferably methylene chloride) or tert-butanol, in the presence of inorganic or organic acid, according to M. A. Umbreit and K. B. Sharpless, J. Amer. Chem. Soc. (1977), 99, 5526.

The compounds of formula (IV) can be obtained by dehydration of a 2-aryl-2-propanol compound of formula:

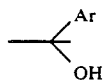     (V)

in which Ar, $R_1$ and m or p have the same meaning as in the general definition of the invention, using dehydrating agents such as $P_2O_5$, $KHSO_4$, $POCl_3$/pyridine and others, according to J. March, ibid. p. 901-903.

The compounds of formula (V) can be prepared by bringing acetophenone or acetylpyridine or an acid derivative of formula:

     (VI)

in which Ar, $R_1$ and m or p have the same meaning as in the general definition of the invention and W is methyl, alkoxy (corresponding benzoic ester) or chlorine, into contact with one or two equivalents of methylmagnesium halide according to J. March, ibid. p. 816-822.

The compounds of formula (VI) are obtained in a manner which is known per se. The compounds of formula (III) can be prepared by reduction of the corresponding sulphonyl halides (generally a chloride) with zinc, with sodium or potassium iodide and with sodium sulphite, according to J. March, ibid. p. 445-446 and W. E. Truce and A. H. Murphy, Chem Rev. (1951), 48, 69. The sulphonyl halides can be prepared according to J. March, ibid. p. 1172.

The compounds of formula (III) can also be prepared by reaction of an organometallic (usually lithium) compound of formula:

$$M(CH_2)_fB \quad \text{(IIIA)}$$

f and B having the same meaning as that shown in the definition of the invention, M being especially lithium, with sulphur dioxide $SO_2$, at a temperature of between −78° C. and 20° C. (preferably −78° C. to −40° C.) in the absence or in the presence of an aprotic solvent such as ethyl ether or tetrahydrofuran, according to H. W. Pinnick and M. A. Reynolds, J. Org. Chem. (1979), 44, 160 and J. March, ibid. p. 550.

The compounds of formula (IIIA) are obtained in a manner which is known per se.

Method B

The compounds of formula (IA) in which n=0, 1 or 2 can be prepared by reaction of the alkali metal salt of an aryl or alkyl thiolate of formula:

$$M'S(CH_2)_fB \quad \text{(VII)}$$

in which M' is an alkali metal or alkaline-earth metal atom, especially sodium or potassium, f and B having the same definition as that shown in the definition of the invention, with a compound of formula (II) where T is halogen, described above, in a protic or aprotic inert solvent such as ketones, alcohols, tetrahydrofuran, acetonitrile or aprotic dipolar solvents such as dimethylformamide, at a temperature of 0° C. to 80° C., (generally 25° C. to 60° C.) in a molar ratio II:VII which is generally between 1 and 10 (preferably 1 and 2).

The sulphide thus obtained (n=0) can be oxidized to sulphoxide (n=1) using one equivalent of oxidizing agent at a temperature of −70° C. to 5° C. (generally 0° C.) or can be oxidized to sulphone (n=2) using two or more equivalents of oxidizing agent at a temperature of 0° C. to 60° C. (generally 10° C. to 30° C.) using numerous oxidizing agents such as $KMnO_4$, $H_2O_2$, $CH_3CO_3H$, perbenzoic acids, $KHSO_5$, and others, using very numerous known methods: J. March, ibid. p. 1089-1090 and B. M. Trost and R. Braslau, J. Org. Chem (1988), 53, 532.

Another subject of the invention is the new products (II) to (VII) which can be used for making use of the process just described.

The following examples illustrate the invention.

EXAMPLE 1

2-Phenyl-1-phenylsulphonyl-2-propene (10.3 g, 0.04 moles) is dissolved in chloroform (100 cc). Bromine (6.8 g, 0.042 moles) is then added dropwise until the colour persists. The organic phase is washed with a 5% solution of sodium thiosulphate (50 cc), water (50 cc) and is dried over $MgSO_4$. After evaporation, a colourless oil (18.8 g) is obtained. This oil is dissolved in a mixture of chloroform (20 cc) and ether (40 cc) and is stored overnight at −18° C. White crystals of 1,2-dibromo-2-phenyl-3-phenylsulphonylpropane (14.3 g, 86%) are filtered off. Mp=74° C.

EXAMPLE 2

2-Phenyl-1-phenylsulphonyl-2-propene (2.6 g, 0.01 mole) is dissolved in chloroform (20 cc). The solution is cooled to 5° C. and chlorine iodide (1.8 g, 0.011 moles) in solution in chloroform (5 cc) is added dropwise. The mixture is stirred at 5° C. for two hours and is then treated in the same way as in Example 1. Evaporation leaves a yellow oil (5.3 g). This oil is dissolved in ether (7.5 cc) and is stored overnight at −18° C. Off-white crystals of 2-chloro-1-iodo-2-phenyl-3-phenylsulphonylpropane (3.3 g, 78%) are filtered off. Mp=75.5° C. (dec.).

EXAMPLE 3

2-Phenyl-1-phenylsulphonyl-2-propene (2.6 g, 0.01 mole) is suspended in a mixture of acetic acid (50 cc) and 35% hydrochloric acid (10 cc). Chlorine is then introduced into the reaction mixture until the allyl sulphone has completely dissolved (5 min). The mixture is poured into ice and water (250 g) and is stirred vigorously until a resin forms.

The resin is filtered off and dissolved in methylene chloride (100 cc) and the organic phase is washed with a 10% sodium carbonate solution (100 cc), water (2×100 cc) and is dried over MgSO$_4$. Evaporation leaves a yellow oil (4.8 g). This oil is dissolved in ether (20 cc) and is stored overnight at −18° C. After filtration and recrystallization from ethanol, pale yellow crystals of 1,2-dichloro-2-phenyl-3-phenylsulphonylpropane (1.2 g, 36%) are obtained. Mp=95° C.

EXAMPLE 4

2-Phenyl-1-phenylsulphonyl-2-propene (2.6 g, 0.01 mole) is suspended in acetic acid (50 cc). Lithium chloride (2 g, 0.05 moles) and 35% hydrochloric acid (5 cc) are then added and, finally, N-bromosuccinimide (1.8 g, 0.01 mole). The mixture is stirred until dissolved (15 min) and is then treated in the same way as in Example 3. Evaporation leaves a yellow oil (3.6 g) which is redissolved in ether (10 cc) and stored overnight at −18° C. White crystals of 1-bromo-2-chloro-2-phenyl-3-phenylsulphonylpropane (1.5 g, 40%) are filtered off. Mp=91° C.

EXAMPLE 5

Using the same method as in Example 1, 2-(6-chloro-2-pyridyl)-1-phenylsulphonyl-2-propene (1.0 g, 0.0035 moles) is treated with bromine (0.6 g, 0.0038 moles) in chloroform. After treatment, evaporation leaves an oil (1.6 g) which is crystallized from ether (40 cc) overnight at −18° C. White crystals of 1,2-dibromo-2-(6-chloro-2-pyridyl)-3-phenylsulphonylpropane (1.2 g, 75%) are filtered off. Mp=119° C.

EXAMPLE 6

Using the same method as in Example 1, 2-(6-chloro-2-pyridyl)-1-cyclopropylsulphonyl-2-propene (1.4 g, 0.0054 moles) is treated with bromine (0.87 g, 0.0054 moles) in chloroform. After treatment, evaporation leaves an oil (2.1 g), which is chromatographed on silica (eluent: 80/20 heptane/chloroform) to give crystals of 1,2-dibromo-2-(6-chloro-2-pyridyl)-3-cyclopropylsulphonylpropane (0.7 g, 31%). Mp=75° C. The compounds brought together in the table below were prepared according to the method of Example 1.

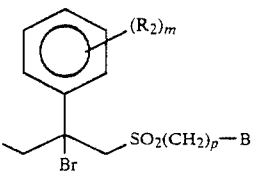

| Example | R1 | f | B | Mp (solvent) $n_D$ (temperature) |
|---------|------|---|--------------|------------------------------|
| 7 | 2-F | 0 | phenyl | 123° C. (CHCl$_3$/pentane) |
| 8 | 4-Me | 0 | phenyl | 101° C. (CHCl$_3$/Et$_2$O) |
| 9 | 4-F | 0 | phenyl | 103° C. (CHCl$_3$/Et$_2$O) |
| 10 | 3,5-diCl | 0 | phenyl | 135° C. (CHCl$_3$/Et$_2$O) |
| 11 | H | 1 | phenyl | 93° C. (CHCl$_3$/Et$_2$O) |
| 12 | H | 0 | 4-F phenyl | 103° C. (CHCl$_3$/pentane) |
| 13 | H | 0 | 2-Cl phenyl | 120° C. (CHCl$_3$/pentane) |
| 14 | H | 0 | 2-F phenyl | 82° C. (Et$_2$O) |
| 15 | H | 0 | 2-Me phenyl | 74° C. (CHCl$_3$/Et$_2$O) |
| 16 | H | 0 | 3-Me phenyl | 95° C. (CHCl$_3$/Et$_2$O) |
| 17 | H | 0 | 2-Cl 4-F phenyl | 110° C. (Et$_2$O/pentane) |
| 18 | 3-Cl | 0 | 2-Cl phenyl | 87° C. (CH$_2$Cl$_2$/iPr$_2$O) |
| 19 | 3-F | 0 | 2-Cl phenyl | 97° C. (Et$_2$O/pentane) |
| 20 | 3-CF$_3$ | 0 | 2-Me phenyl | 92° C. (Et$_2$O) |
| 21 | 3,5-diCl | 0 | 4-F phenyl | 133.5° C. (CHCl$_3$/Et$_2$O) |
| 22 | 3,5-diCl | 0 | 2-Me phenyl | 117° C. (chromatography) |
| 23 | H | 0 | (CH$_2$)$_3$CH$_3$ | 1.5768 (25° C.) |
| 24 | H | 0 | cyclopropyl | 95° C. (Et$_2$O) |
| 25 | 3-Cl | 0 | CH(CH$_3$)$_2$ | 1.5717 (24° C.) |

Preparation of 2-phenyl-1-phenylsulphonyl-2-propene

2-Phenyl-1-propene (130 cc, 1 mole) is dissolved in methylene chloride (1,500 cc). Water (300 cc) and calcium hypochlorite (101.5 g, 0.5 moles) containing 70% of active chlorine are added. Solid carbon dioxide is added for 2 hours with very energetic stirring. The two phases are separated and the organic phase is dried over MgSO$_4$.

After evaporation, a yellow oil (145 g) is obtained. NMR analysis (60 MHz) shows the presence of 45% of 1-chloro-2-phenyl-2-propene, 45% of 1-chloro-2-phenyl-1-propene and 10% of 1-chloro-2-phenyl-2-propanol.

This mixture (17 g, 0.05 moles as 1-chloro-2-phenyl-2-propene) is dissolved in dimethylformamide (100 cc). Sodium benzenesulphinate (8.2 g, 0.05 moles) is added and the mixture is heated to 70° C. for 2 h. The reaction mixture is poured into ice and water (350 g). It is stirred vigorously with pentane (150 cc) to extract the unreacted 1-chloro-2-phenyl-1-propene and 1-chloro-2-phenyl-2-propanol for 15 to 30 min until crystallization is complete. The crystals formed are filtered off, are washed with pentane (50 cc) and diisopropyl ether (50 cc), are drained thoroughly and are dried. 2-Phenyl-1-phenylsulphonyl-2-propene (9.8 g, 76%) is obtained. Mp=105° C.

The following compounds were prepared in the same way:

2-(2-fluorophenyl)-1-phenylsulphonyl-2-propene, mp=95° C.,
2-(4-methylphenyl)-1-phenylsulphonyl-2-propene, mp=92° C.,
2-(4-fluorophenyl)-1-phenylsulphonyl-2-propene, mp=85° C.,
2-(3-chlorophenyl)-1-(2-chlorophenylsulphonyl)-2-propene, mp=87° C.,
1-(2-chlorophenylsulphonyl)-2-phenyl-2-propene, $n^{22}=1.6090$,
2-(3,5-dichlorophenyl)-1-phenylsulphonyl-2-propene, mp=98° C.,
1-(2-chlorophenylsulphonyl)-2-(3-fluorophenyl)-2-propene, $n_D^{24}=1.5860$,
1-(2-fluorophenylsulphonyl)-2-phenyl-2-propene, mp=84° C.,
1-butylsulphonyl-2-phenyl-2-propene, mp=25° C.,
1-cyclopropylsulphonyl-2-phenyl-2-propene, mp=76° C.

Preparation of 1-benzylsulphonyl-2-phenyl-2-propene

Potassium carbonate (27 g, 0.19 moles) is suspended in acetone (600 cc). The mixture is heated to 60° C. and is degassed with nitrogen. A mixture of benzyl mercaptan (21.7 g, 0.17 moles) and the allyl chloride (59 g, 0.17 moles as 1-chloro-2-phenyl-2-propene) prepared according to the preceding example, in solution in acetone (175 cc) is added dropwise at 60° C. The mixture is stirred at 60° C. for two hours.

The reaction mixture is poured into ice and water (2,000 g) and is reextracted with ether (3×500 cc). The organic phase is washed with water until neutral and is dried over MgSO₄. Evaporation leaves a yellow oil (82.5 g), which is chromatographed on silica (eluent heptane, then 99/1 heptane/chloroform) to give 1-benzylthio-2-phenyl-2-propene (19.5 g, 46%). Colourless oil. $n_D^{25}=1.6041$.

1-Benzylthio-2-phenyl-2-propene (13.2 g, 0.055 moles) is dissolved in methanol (300 cc) and water (300 cc). Oxone (36.9 g, 0.12 moles as HKSO₅) is added portionwise and the mixture is stirred at ambient temperature for three hours. The reaction mixture is diluted with water (1,000 cc), pentane (100 cc) is added, and the mixture is stirred vigorously until crystallization takes place. White crystals of 1-benzylsulphonyl-2-phenyl-2-propene (10.7 g, 72%) are obtained by filtration followed by drying. Mp=118° C.

The following compounds were prepared in the same way:

2-(3-chlorophenyl)-1-isopropylsulphonyl-2-propene, $n_D^{25}=1.5715$,
1-(4-fluorophenylsulphonyl)-2-phenyl-2-propene, mp=83° C.,
1-(3-methylphenylsulphonyl)-2-phenyl-2-propene, mp=61° C.
1-(2-methylphenylsulphonyl)-2-phenyl-2-propene, mp=62° C.,
1-(2-chloro-4-fluorophenylsulphonyl)-2-phenyl-2-propene, mp=64° C.,
2-(3,5-dichlorophenyl)-1-(4-fluorophenylsulphonyl)-2-propene, mp=105° C.,
2-(3,5-dichlorophenyl)-1-(2-methylphenylsulphonyl)-2-propene, mp=72° C., 1-(2-methylphenylsulphonyl)-2-(3-trifluoromethylphenyl)-2-propene, mp=51° C.

Preparation of 2-(6-chloro-2-pyridyl)-1-phenyl-sulphonyl-2-propene 2-(6-Chloro-2-pyridyl)-1-propene (15.3 g, 0.1 mole) is dissolved in 1,2-dichloroethane (200 cc). Bis(4-chlorophenyl) diselenide (0.5 g, catalytic) and N-chlorosuccinimide (14.7 g, 0.11 moles) are added and heated to 60° C. for 24 hours. The reaction mixture is concentrated down to one third, the succinimide is filtered off and the organic phase is washed with water (2×200 cc), with a 15% solution of sodium bicarbonate (1×200 cc) and water (2×200 cc) and is dried over MgSO₄. Crude: 13.9 g.

NMR analysis (60 MHz) shows the presence of 55% of 1-chloro-2-(6-chloro-2-pyridyl)-2-propene and 45% of 1-chloro-2-(6-chloro-2-pyridyl)-1-propene.

In a similar manner to the preparation of 2-phenyl-1-phenylsulphonyl-2-propene, this mixture (7 g, 0.02 moles as 1-chloro-2-(6-chloro-2-pyridyl)-2-propene) is treated with sodium benzenesulphinate to obtain, after treatment, 2-(6-chloro-2-pyridyl)-1-phenylsulphonyl-2-propene (4.3 g, 73%). Mp=135° C.

The following compound was prepared in the same way:

2-(6-chloro-2-pyridyl)-1-cyclopropylsulphonyl-2-propene, $n_D^{24}=1.5730$.

The invention also relates to the use of the compounds of formula (I) as a herbicide. As weeds which can be controlled or destroyed using the compounds of formula (I) there may be mentioned:

| Abbreviation | Graminaceae/Cyperaceae | |
|---|---|---|
| | Latin name | English name |
| AVE | *Avena fatua* | Wild oat |
| ECH | *Echinochloa crusgalli* | Panic grass |
| LOL | *Lolium multiflorum* | Italian ryegrass |
| CYP | *Cyperus esculentus* | Chufa flat sedge |
| DIG | *Digitaria sanguinalis* | Hairy fingergrass |
| ALO | *Alopercurus myosuroides* | Slender foxtail |

Most of the time, the compounds of formula (I) are employed in the form of a herbicidal composition comprising one or more agriculturally acceptable carriers.

In fact, for their practical use, the compounds according to the invention are rarely employed by themselves. In most cases these compounds form part of compositions. These compositions, which can be employed as herbicidal agents, contain as active substance a compound according to the invention such as described above mixed with agriculturally acceptable solid or liquid carriers and surface-active agents which are also agriculturally acceptable. In particular, the usual inert carriers and the usual surface-active agents can be employed. These compositions also form part of the invention.

These compositions may also contain all kinds of other ingredients such as, for example, protective colloids, adhesives, thickeners, thixotropic agents, penetrating agents, stabilizers, sequestrants and the like. More generally, the compounds employed in the invention may be used in combination with any of the solid or liquid additives corresponding to the usual formulation techniques.

As a general rule, the compositions according to the invention usually contain approximately from 0.05 to 95% (by weight) of a compound according to the invention, one or more solid or liquid carriers and, optionally, one or more surface-active agents.

In the present description the term "carrier" denotes a natural or synthetic, organic or inorganic substance with which the compound is combined to facilitate its application to the plant, to seed or to the soil. This carrier is therefore generally inert and it must be agriculturally acceptable, especially on the treated plant. The carrier may be solid (clays, natural or synthetic silicates, silica, resins, waxes, solid fertilizers, and the like) or liquid (water, alcohols, especially butanol, and the like).

The surface-active agent may be an emulsifying, dispersing or wetting agent of an ionic or nonionic type or a mixture of such surface-active agents. There may be mentioned, for example, salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols (especially alkylphenols or arylphenols), salts of sulphosuccinic acid esters, taurine derivatives (especially alkyl taurates), phosphoric esters of polycondensates of ethylene oxide with alcohols or phenols, esters of fatty acids and of polyols, and sulphate, sulphonate and phosphate functional derivatives of the above compounds.

The presence of at least one surface-active agent is generally indispensible when the compound and/or the inert carrier are not water-soluble and the vector agent of the application is water.

Thus, therefore, the compositions for agricultural use according to the invention may contain the active substances according to the invention within very wide limits, ranging from $5 \times 10^{-5}\%$ to 95% (by weight). Their content of surface-active agent is advantageously between 5% and 40% by weight.

These compositions according to the invention are themselves in fairly diverse solid or liquid forms.

As solid forms of compositions, there may be mentioned dusting powders (with a compound content which can go up to 100%) and granulates, especially those obtained by extrusion, by compacting, by impregnation of a granulated carrier or by granulation starting with a powder (the content of compound in these granulates being between 0.5 and 80% in these latter cases).

The wettable powders (or spraying powder) are usually prepared so that they contain 20 to 95% of active substance, and they usually contain, in addition to the solid carrier, from 0 to 30% of a wetting agent, from 3 to 20% of a dispersing agent and, when necessary, from 0 to 10% of one or more stabilizers and/or other additives, such as penetrating agents, adhesives or anticaking agents, colorants, and the like.

To obtain the spraying powders or wettable powders, the active substances are mixed intimately with the additional substances in suitable mixers and are ground up using mills or other suitable grinders. This yields spraying powders whose wettability and suspendability are advantageous; they can be made into a suspension with water at any desired concentration, and these suspensions can be employed very advantageously, in particular for application to plant foliage.

Pastes can be produced instead of the wettable powders. The conditions and methods of production and of use of these pastes are similar to those of the wettable powders or spraying powders.

By way of example, here are various compositions of wettable powders (or spraying powders):

EXAMPLE F 1

| | |
|---|---|
| active substance (compound No. 1) | 50% |
| fatty alcohol/ethylene oxide condensate (wetting agent) | 2.5% |
| phenylethylphenol/ethylene oxide condensate (dispersing agent) | 5% |
| chalk (inert carrier) | 42.5% |

EXAMPLE F 2

| | |
|---|---|
| active substance (compound No. 1) | 10% |
| syntheic oxo $C_{13}$ alcohol of branched type, condensed with 8 to 10 ethylene oxides (wetting agent) | 0.75% |
| neutral calcium lignosulphonate (dispersing agent) | 12% |
| calcium carbonate (inert filler) | q.s. 100% |

EXAMPLE F 3

This wettable powder contains the same ingredients as in the preceding example, in the following proportions:

| | |
|---|---|
| active substance | 75% |
| wetting agent | 1.50% |
| dispersing agent | 8% |
| calcium carbonate (inert filler) | q.s. 100% |

EXAMPLE F 4

| | |
|---|---|
| active substance (compound No. 1) | 90% |
| fatty alcohol/ethylene oxide condensate (wetting agent) | 4% |
| phenylethylphenol/ethylene oxide condensate (dispersing agent) | 6% |

EXAMPLE F 5

| | |
|---|---|
| active substance (compound No. 1) | 50% |
| mixture of anionic and nonionic surfactants (wetting agent) | 2.5% |
| sodium lignosulphonate (dispersing agent) | 5% |
| kaolin clay (inert carrier) | 42.5% |

The compounds according to the invention can be formulated in the form of water-dispersible granulates which are also included within the scope of the invention.

These dispersible granulates, with an apparent density which is generally between approximately 0.3 and 0.6, have a particle size which is generally between approximately 150 and 2,000 and preferably between 300 and 1,500 microns.

The content of active substance in these granulates is generally between approximately 1% and 90%, and preferably between 25% and 90%.

The remainder of the granulate is essentially made up of a solid filler and optionally of surface-active adjuvants endowing the granulate with properties of dispersibility in water. These granulates can be essentially of two distinct types, depending on whether the filler contained is or is not water-soluble. When the filler is water-soluble, it may be inorganic or, preferably, organic. Excellent results have been obtained with urea. In the case of an insoluble filler, the latter is preferably inorganic, such as, for example, kaolin or bentonite. It is then advantageously accompanied by surface-active agents (in a proportion of 2 to 20% by weight of the granulate) more than half of which consists, for example, of at least one essentially anionic dispersing agent such as an alkali metal or alkaline-earth metal polynaphthalenesulphonate or an alkali metal or alkaline-earth metal lignosulphonate, the remainder consisting of non-ionic or anionic wetting agents, such as an alkali metal or alkaline-earth metal alkylnaphthalenesulphonate.

Furthermore other adjuvants, such as antifoaming agents, may be added, although this is not essential.

The granulate according to the invention may be prepared by mixing the necessary ingredients, followed by granulation according to a number of techniques which are known per se (pelletizer, fluid bed, sprayer, extrusion, and the like). The finishing step is generally crushing followed by screening to the chosen particle size within the limits noted above.

It is preferably obtained by extrusion, the operation being carried out as indicated in the examples below.

EXAMPLE F 6

Dispersible Granulates

90% by weight of active substance (compound No. 1) and 10% of urea pearls are mixed in a blender. The mixture is then ground in a pin mill. A powder is obtained, which is moistened with approximately 8% by weight of water. The moist powder is extruded in an extruder with a perforated roller. A granulate is obtained, which is dried and then crushed and screened, so as to retain only granules of a size between 150 and 2,000 microns respectively.

EXAMPLE F 7

Dispersible Granulates

The following constituents are mixed in a blender:

| active substance (compound No. 1) | 75% |
|---|---|
| wetting agent (sodium alkylnaphthalene-sulphonate) | 2% |
| dispersing agent (sodium polynaphthalene-sulphonate) | 8% |
| water-insoluble inert filler (kaolin) | 15% |

This mixture is granulated in a fluid bed, in the presence of water, and is then dried, crushed and screened so as to obtain granules of size between 0.15 and 0.80 mm.

These granulates can then be employed by themselves, in solution or in dispersion in water, so as to obtain the required dose. They can also be employed to prepare combinations with other active substances, especially fungicides, the latter being in the form of wettable powders or of granulates or aqueous suspensions.

The compounds of formula (I) can, furthermore, be employed in the form of dusting powders; it is also possible to employ a composition comprising 50 g of active substance and 950 g of talc; it is also possible to employ a composition comprising 20 g of active substance, 10 g of finely divided silica and 970 g of talc; these constituents are mixed and ground and the mixture is applied by dusting.

As forms of compositions which are liquid or intended to constitute liquid compositions when applied, there may be mentioned solutions, in particular water-soluble concentrates, emulsifiable concentrates, emulsions, concentrated suspensions, aerosols, wettable powders (or spraying powder) and pastes.

Emulsifiable or soluble concentrates in most cases contain 10 to 80% of active substance, while emulsions or solutions which are ready for use contain 0.001 to 20% of active substance.

In addition to the solvent, the emulsifiable concentrates may, when necessary, contain 2 to 20% of suitable additives such as stabilizers, surface-active agents, penetrating agents, corrosion inhibitors, colorants or the adhesives referred to above.

From these concentrates it is possible, by dilution with water, to obtain emulsions of any desired concentration, which are particularly suitable for application to crops.

By way of example, here is the composition of some emulsifiable concentrates:

EXAMPLE F 8

| active substance | 400 g/l |
|---|---|
| alkali metal dodecylbenzenesulphonate | 24 g/l |
| nonylphenol condensate with 10 molecules of ethylene oxide | 16 g/l |
| cyclohexanone | 200 g/l |
| aromatic solvent | q.s. 1 liter |

According to another emulsifiable concentrate formulation, the following are employed:

EXAMPLE F 9

| active substance | 250 g |
|---|---|
| epoxidized vegetable oil | 25 g |
| mixture of alkylarylsulphonate and of polyglycol ether and of fatty alcohols | 100 g |
| dimethylformamide | 50 g |
| xylene | 575 g |

Flowables, which can also be applied by dusting, are prepared so as to obtain a stable fluid product which does not settle and usually contain from 10 to 75% of active substance, from 0.5 to 15% of surface-active agents, from 0.1 to 10% of thixotropic agents, from 0 to 10% of suitable additives, such as antifoams, corrosion inhibitors, stabilizers, penetrating agents and adhesives and, as carrier, water or an organic liquid in which the active substance is poorly soluble or insoluble: certain organic solid substances or inorganic salts can be dissolved in the carrier to help prevent settling or as antifreezes for the water.

By way of example, here is a flowable composition:

EXAMPLE F 10

| compound | 500 g |
|---|---|
| polycondensate of ethylene oxide with tristyrylphenol phosphate | 50 g |
| alkylphenol/ethylene oxide polycondensate | 50 g |
| sodium polycarboxylate | 20 g |
| ethylene glycol | 50 g |
| organopolysiloxane oil (antifoam) | 1 g |
| polysaccharide | 0.5 g |
| water | 316.5 g |

Aqueous dispersions and emulsions, for example the compositions obtained by diluting a wettable powder or an emulsifiable concentrate according to the invention with water, are included within the general scope of the present invention. The emulsions may be of the water-in-oil or oil-in-water type and may have a thick consistency like that of a mayonnaise.

As for compositions which are adapted to storage and to transport, these more advantageously contain from 0.5 to 95% (by weight) of active substance.

The present invention also relates to a weeding method (especially of monocotyledon crop areas (wheat, corn, rice)), which consists in applying an effective quantity of a compound of formula (I) to the plants which are to be destroyed.

During the application to a cultivated area, the application dosage should be sufficient to control the generation of adventitious plants without occasioning permanent substantial damage to the said crops. In this context, then, an effective dosage means the dosage which enables this result to be obtained.

The products and compositions according to the invention are preferably applied to areas or terrains where it is desired to prevent the growth or the development of plants which have not yet grown (preemergence application). Nevertheless it will also be possible to employ a weeding method which consists in applying an effective quantity of a compound of formula (I) to the weeds to be removed when the latter have a green foliage, advantageously the monocotyledons.

It is possible to operate so that the crop is sown before or after the treatment.

The application dosage of active substance is generally between 1 and 8,000 g/ha.

The following examples illustrate the invention:

EXAMPLE A

Herbicidal Application During Preemergence of Plant Species

A number of seeds, determined depending on the plant species and the seed size, are sown in 7×7×8 cm pots filled with light agricultural soil.

The pots are treated by spraying with a spraying mixture in a quantity corresponding to a volume application rate of 500 l/ha and containing the active ingredient at the desired concentration.

The treatment with the spraying mixture is therefore applied to seeds which are not covered with earth (the term spraying mixture is employed to denote generally water-diluted compositions, as applied to the plants).

The spraying mixture employed for the treatment is a solution or suspension of the active ingredient in a water/acetone mixture in proportions of 50/50, in the presence of 0.05% by weight of Cemulsol NP 10 (surface-active agent, consisting of a polycondensate of ethylene oxide and alkylphenol, especially of a polycondensate of ethylene oxide and nonylphenol) and 0.04% by weight of Tween 20 (surface-active agent consisting of an oleate of a polycondensate of ethylene oxide derived from sorbitol).

In the case of a suspension, the latter is obtained by mixing and milling the ingredients in a micronizer so as to obtain a mean particle size of less than 40 microns.

After treatment, the seeds are covered with a layer of earth approximately 3 mm in depth.

The pots are then placed in troughs intended to receive the moistening water by subirrigation, and are maintained for 24 days at room temperature under 70% relative humidity.

Scoring of the Herbicidal Activity

The recording is carried out as follows: at the end of 24 days, a percentage (D) of destruction of the number of shoots in the treated pots is measured in relation to the number of plants in the untreated (control) pots. The remaining treated plants are used to measure the percentage of reduction in size (RS) relative to the control plants.

The percentage of foliage volume not destroyed by the product is therefore given by the formula:

$$\frac{[100 - D] \times [100 - RS]}{100} = A$$

This value A is converted into a score from 0 to 5 according to the following scale:

| | Score |
|---|---|
| 0 to 10 | 5 (complete destruction) |
| 10 to 30 | 4 |
| 30 to 50 | 3 |
| 50 to 70 | 2 |
| 70 to 90 | 1 |
| 90 to 100 | 0 (no effect) |

The results obtained are shown after Example B for application rates of 4,000 g/ha.

EXAMPLE B

Herbicidal Application During Postemergence of Plant Species

A number of seeds, determined depending on the plant species and the seed size, are sown in 7×7×8 cm pots filled with light agricultural soil.

The seeds are then covered with a layer of soil approximately 3 mm in depth and the seed is left to germinate until it gives rise to a plantlet at the appropriate stage. The treatment stage for graminaceous plants is the "second leaf being formed" stage. The treatment stage for dicotyledon plants is the "cotyledons open, first true leaf being developed" stage.

The pots are then treated by spraying with a spraying mixture in a quantity corresponding to a volume application rate of 500 l/ha and containing the active ingredient at the desired concentration.

The spraying mixture has been prepared in the same way as in Example A.

The treated pots are next placed in troughs intended to receive the moistening water by subirrigation, and are maintained for 24 days at room temperature under 70% relative humidity.

Scoring of the Herbicidal Activity

The recording is carried out as follows: at the end of 24 days, a percentage (D) of destruction of the number of shoots in the treated pot is measured in relation to the number of plants in the untreated (control) pots. The remaining treated plants are used to measure the percentage of reduction in size (RS) relative to the control plants.

The percentage of foliage volume not destroyed by the product is therefore given by the formula:

$$\frac{[100 - D] \times [100 - RS]}{100} = A$$

This value A is converted into a score from 0 to 5 according to the following scale:

|  | Score |
|---|---|
| 0 to 10 | 5 (complete destruction) |
| 10 to 30 | 4 |
| 30 to 50 | 3 |
| 50 to 70 | 2 |
| 70 to 90 | 1 |
| 90 to 100 | 0 (no effect) |

The results obtained are shown after Table A for application rates of 4,000 g/ha The plant species employed in these Examples A and B are:

| ABBREVIATIONS | LATIN NAME | ENGLISH NAME |
|---|---|---|
| AVE | *Avena fatua* | Wild oat |
| ALO | *Alopercurus myosuroides* | Slender foxtail |
| ECH | *Echinochloa crusgalli* | Panic grass |
| CYP | *Cyperus esculentus* | Chufa flat sedge |
| DIG | *Digitaria sanguinalis* | Hairy fingergrass |

HERBICIDAL ACTIVITY AT PREEMERGENCE

| COMPOUNDS NO. | AVE | ECH | DIG | CYP | ALO |
|---|---|---|---|---|---|
| 1 | 5 | 5 | 5 | 3 | — |
| 2 | 1 | 4 | 4 | 0 | — |
| 4 | 5 | 5 | 5 | 3 | 5 |
| 8 | 2 | 4 | 5 | 1 | 2 |
| 9 | 5 | 5 | 5 | 3 | 4 |
| 11 | 1 | 5 | 5 | 3 | 5 |
| 12 | 5 | 5 | 5 | 3 | 5 |
| 13 | 5 | 5 | 5 | 2 | 5 |
| 14 | 4 | 5 | 5 | 4 | 5 |
| 15 | 5 | 5 | 5 | 3 | 5 |
| 16 | 3 | 5 | 5 | 3 | 5 |
| 17 | 3 | 5 | 5 | 3 | 5 |
| 23 | 0 | 5 | 5 | 1 | 5 |
| 24 | 5 | 5 | 5 | 2 | 5 |
| 25 | 5 | 5 | 5 | 3 | 5 |

HERBICIDAL ACTIVITY AT POSTEMERGENCE

| COMPOUNDS NO. | ECH | DIG | ALO |
|---|---|---|---|
| 11 | 0 | 3 | 3 |
| 13 | 4 | 3 | 2 |
| 15 | 5 | 3 | 3 |
| 16 | 3 | 0 | 3 |
| 17 | 3 | 0 | 3 |
| 24 | 3 | 1 | 3 |

EXAMPLE C

Test for Selectivity in Major Crops with Herbicidal Application During Preemergence of the Plant Species A number of seeds, determined depending on the plant species and the seed size, are sown in 7×7×8 cm pots filled with light agricultural soil.

The seeds are then covered with a layer of soil approximately 3 mm in depth.

The pots are then treated by spraying with a spraying mixture in a quantity corresponding to a volume application rate of 500 l/ha and containing the active ingredient at the desired concentration.

The spraying mixture has been prepared in the same way as in Example A.

The treated pots are then placed in troughs intended to receive the moistening water by subirrigation and are maintained for 24 days at room temperature under 70% relative humidity.

Scoring of the Herbicidal Activity

The recording is carried out as follows: at the end of 24 days, a percentage (D) of destruction of the number of shoots in the treated pot is measured in relation to he number of plants in the untreated (control) pots. The remaining treated plants are used to measure the percentage of reduction in size (RS) relative to the control plants.

The percentage of foliage volume not destroyed by the product is therefore given by the formula:

$$\frac{[100 - D] \times [100 - RS]}{100} = A$$

This value A is converted into a score from 0 to 5 according to the following scale:

|  | Score |
|---|---|
| 0 to 10 | 5 (complete destruction) |
| 10 to 30 | 4 |
| 30 to 50 | 3 |
| 50 to 70 | 2 |
| 70 to 90 | 1 |
| 90 to 100 | 0 (no effect) |

Thus, a product is judged to be selective in respect of the crop when the scored value A is 0 or 1.

The results obtained are shown in Example C for application rates of 1 or 2 or 4 kg of active ingredient per hectare, depending on the products.

The plant species employed in this example are:

(1) In the case of the adventitious plants

| ABBREVIATIONS | LATIN NAME | ENGLISH NAME |
|---|---|---|
| ECH | *Echinochloa crus-galli* | Panic grass |
| DIG | *Digitaria snaguinalis* | Hairy fingergrass |
| SOR | *Sorghum halepense* | Johnson grass |
| SET | *Setaria faberii* | Giant foxtail |

(2) In the case of the crops

| ABBREVIATIONS | LATIN NAME | ENGLISH NAME |
|---|---|---|
| TRZ | *Triticum aestivum* | Spring wheat |
| ZEA | *Zea mays* | Maize |
| ORY | *Oryza sativa* | Rice |
| GLX | *Glycine maximum* | Soybean |

| COMPOUNDS NO. | DOSE APPLIED (kg/ha) | TEST FOR SELECTIVITY IN MAJOR CROPS HERBICIDAL ACTIVITY AT PREEMERGENCE | | | | | | | |
|---|---|---|---|---|---|---|---|---|---|
|  |  | ECH | DIG | SOR | SET | TRZ | ZEA | ORY | GLY |
| 1 | 2 | 3 | 5 | 5 | 2 | 0 | 0 | 0 | 1 |
| 4 | 2 | 5 | 5 | 1 | 5 | 0 | 0 | 1 | 0 |
| 9 | 2 | 5 | 5 | 2 | 2 | 0 | 0 | 3 | 0 |

| | | | | | | | | |
|---|---|---|---|---|---|---|---|---|
| 13 | 2 | 4 | 5 | 2 | 4 | 0 | 1 | 2 | 0 |
| 14 | 2 | 3 | 5 | 3 | 4 | 0 | 2 | 0 | 0 |
| 15 | 2 | 5 | 5 | 5 | 5 | 1 | 0 | 3 | 0 |

As can be seen from the table of results of this Example C, many products exhibit an excellent antigraminaceous activity at preemergence while showing an excellent selectivity for 1 or 2 or 3 or 4 of the 4 tested crops=wheat, maize, rice, soybean.

We claim:

1. A method of inhibiting the growth of a weed which comprises administering to said weed a herbicidally effective amount of a compound of the formula:

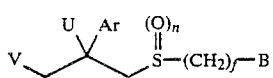

wherein:
$n = 0, 1, 2$
$f = 0, 1$
Ar is chosen from the groups

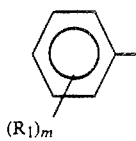
1-Ar

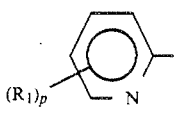
2-Ar

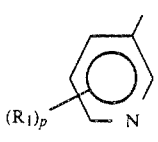
3-Ar

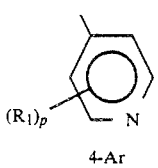
4-Ar

U is a bromine or chlorine atom,
V is a bromine, chlorine or iodine atom,
$R_1$ is a halogen atom, $C_1$-$C_4$ alkyl, $C_1$-$C_4$ alkoxy, $C_1$-$C_4$ haloalkyl, $C_1$-$C_4$ haloalkoxy, nitro or cyano group $C_6$-$C_{10}$ aryl, $C_7$-$C_{11}$ aralkyl, $C_6$-$C_{10}$ aryloxy optionally substituted by 1 or 2 halogen atoms, or $C_7$-$C_{11}$, aralkyloxy optionally substituted by 1 or 2 halogen atoms, $m=0, 1, 2, 3, 4, 5$, $p=0, 1, 2, 3, 4$, the various radicals $R_1$ being identical or different when m or p is greater than or equal to 2, B is chosen from $C_1$-$C_{10}$ alkyl and $C_3$-$C_{10}$ cycloalkyl groups, these groups being optionally substituted by 1 to 6 halogen atoms or chosen from the groups

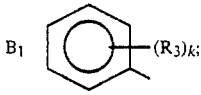

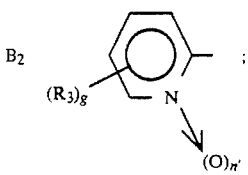

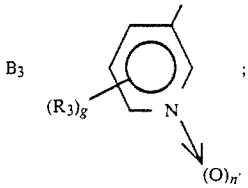

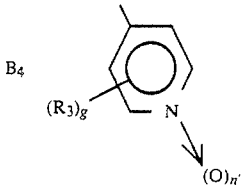

$R_3$ having one of the meanings shown for $R_1$ or $NR_4R_5$, $S(O)_hR_6$, $(C=O)R_7$,
$R_4$ and $R_5$, which are identical or different, are H, $C_1$-$C_4$ alkyl or $C_6$-$C_{10}$ aryl, $R_6$ is $C_1$-$C_4$ alkyl,
$R_7$ is $C_1$-$C_4$ alkyl, $C_1$-$C_4$ alkoxy, $C_1$-$C_4$ haloalkoxy or $NR_9R_{10}$,
$R_9$ and $R_{10}$, which are identical or different, are H or $C_1$-$C_4$ alkyl,
the various radicals $R_3$ being identical or different when
k or g is greater than or equal to 2,
$k = 0, 1, 2, 3, 4, 5$,
$g = 0, 1, 2, 3, 4$,
$h = 1, 2$, and
$n' = 0, 1$, wherein aryl is an aromatic compound containing 6-10 atoms.

2. The method of claim 1 wherein $n=2$.
3. The method of claim 1 wherein U and V correspond to the bromine atom.
4. The method of claim 1 wherein m is smaller than or equal to 3.
5. The method of claim 1 wherein p is smaller than or equal to 2.
6. The method of claim 1 wherein k is smaller than or equal to 2.
7. The method of claim 1 wherein g is smaller than or equal to 1.
8. The method of claim 1 wherein $R_2$ is halogen, nitro, trifluoromethyl, methoxy or methyl.

* * * * *

UNITED STATES PATENT AND TRADEMARK OFFICE
CERTIFICATE OF CORRECTION

PATENT NO. : 5,123,953　　　　　　　　　　　　Page 1 of 2

DATED : June 23, 1992

INVENTOR(S) : Phillipe Desbordes, et al.

It is certified that error appears in the above-identified patent and that said Letters Patent is hereby corrected as shown below:

On title page, item [75], lines 1 & 4,
"Lyons" should read as --Lyon--

On the Title page, Section [73]: "Lyons" should read as --Lyon--

Column 1, line 10: after "postemergence" insert --.--

Column 2, line 55: "n" should read as --n'--

Column 3, lines 66-67: "tempera ture" should read as --temperature--

Column 4, line 35: "dimethoxy-ethane" should read as --dimethoxyethane--

UNITED STATES PATENT AND TRADEMARK OFFICE
CERTIFICATE OF CORRECTION

PATENT NO. : 5,123,953
DATED : June 23, 1992
INVENTOR(S) : Phillipe Desbordes, et al It is certified that error appears in the above-indentified patent and that said Letters Patent is hereby corrected as shown below:

Column 20, line 66, Claim 8: "$R_2$" should read as --$R_1$--

Signed and Sealed this

Twenty-sixth Day of October, 1993

Attest:

BRUCE LEHMAN

Attesting Officer     Commissioner of Patents and Trademarks